US007190998B2

(12) United States Patent
Shalev et al.

(10) Patent No.: US 7,190,998 B2
(45) Date of Patent: *Mar. 13, 2007

(54) METHOD AND APPARATUS FOR STIMULATING THE SPHENOPALATINE GANGLION TO MODIFY PROPERTIES OF THE BBB AND CERBRAL BLOOD FLOW (75) Inventors: Alon Shalev, Raanana (IL); Yossi Gross, Moshav Mazor (IL)

(73) Assignee: Braingate Ltd., Moshay Mazor (IL)

( * ) Notice: Subject to any disclaimer, the term of this patent is extended or adjusted under 35 U.S.C. 154(b) by 221 days.

This patent is subject to a terminal disclaimer.

(21) Appl. No.: 10/753,882

(22) Filed: Jan. 9, 2004

(65) Prior Publication Data
US 2004/0210269 A1    Oct. 21, 2004

Related U.S. Application Data (63) Continuation of application No. 10/258,714, filed as application No. PCT/IL01/00402 on May 7, 2001.

(60) Provisional application No. 60/203,172, filed on May 8, 2000.

(51) Int. Cl.
*A61N 1/00* (2006.01)

(52) U.S. Cl. .......................................................... 607/3

(58) Field of Classification Search .................... 607/2, 607/3
See application file for complete search history.

(56) References Cited

U.S. PATENT DOCUMENTS

| 4,152,928 | A | 5/1979 | Roberts |
| 4,319,580 | A | 3/1982 | Colley et al. |
| 4,886,493 | A | 12/1989 | Yee |
| 4,979,511 | A | 12/1990 | Terry, Jr. et al. |
| 5,031,618 | A | 7/1991 | Mullett |
| 5,154,172 | A | 10/1992 | Terry, Jr. et al. |
| 5,179,950 | A | 1/1993 | Stanislaw |

(Continued)

FOREIGN PATENT DOCUMENTS

WO    WO 97/18855 A1    5/1997

(Continued)

OTHER PUBLICATIONS

Bolay et al., "Intrinsic brain activity triggers trigeminal meningeal afferents in a migraine model," Nature Medicine 8:136-142 (Feb. 2002).

(Continued)

*Primary Examiner*—Scott M. Getzow
(74) *Attorney, Agent, or Firm*—Browdy and Neimark, PLLC (57) ABSTRACT Apparatus for modifying a property of a brain of a patient is provided, including one or more electrodes (7), adapted to be applied to a site selected from a group of sites consisting of: a sphenopalatine ganglion (SPG) (6) of the patient and a neural tract originating in or leading to the SPG. A control unit (8) is adapted to drive the one or more electrodes to apply a current to the site capable of inducing (a) an increase in permeability of a blood-brain barrier (BBB) of the patient, (b) a change in cerebral blood flow of the patient, and/or (c) an inhibition of parasympathetic activity of the SPG.

30 Claims, 8 Drawing Sheets

U.S. PATENT DOCUMENTS

| | | |
|---|---|---|
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,223,254 A | 6/1993 | Paradiso et al. |
| 5,231,988 A | 8/1993 | Wernicke et al. |
| 5,235,980 A | 8/1993 | Varrachio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,304,632 A | 4/1994 | Vaudry et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,531,778 A | 7/1996 | Maschino et al. |
| 5,540,730 A | 7/1996 | Terry, Jr. et al. |
| 5,571,150 A | 11/1996 | Wernicke et al. |
| 5,693,853 A | 12/1997 | Abrahamsson |
| 5,707,400 A | 1/1998 | Terry, Jr. et al. |
| 5,855,907 A | 1/1999 | Peyman |
| 5,928,272 A | 7/1999 | Adkins et al. |
| 5,938,689 A | 8/1999 | Fischell et al. |
| 5,938,690 A | 8/1999 | Law et al. |
| 6,006,124 A | 12/1999 | Fischell et al. |
| 6,016,449 A | 1/2000 | Fischell et al. |
| 6,061,593 A | 5/2000 | Fischell et al. |
| 6,128,538 A | 10/2000 | Fischell et al. |
| 6,134,474 A | 10/2000 | Fischell et al. |
| 6,161,045 A | 12/2000 | Fischell et al. |
| 6,230,049 B1 | 5/2001 | Fischell et al. |
| 6,232,326 B1 | 5/2001 | Nelson |
| 6,277,841 B1 | 8/2001 | Rajagopalan et al. |
| 6,353,754 B1 | 3/2002 | Fischell et al. |
| 6,354,299 B1 | 3/2002 | Fischell et al. |
| 6,360,122 B1 | 3/2002 | Fischell et al. |
| 6,405,079 B1 | 6/2002 | Ansarinia |
| 6,410,046 B1 | 6/2002 | Lerner |
| 6,427,086 B1 | 7/2002 | Fischell et al. |
| 6,432,986 B2 | 8/2002 | Levin |
| 6,459,936 B2 | 10/2002 | Fischell et al. |
| 6,466,822 B1 | 10/2002 | Pless |
| 6,473,639 B1 | 10/2002 | Fischell |
| 6,473,644 B1 | 10/2002 | Terry, Jr. et al. |
| 6,480,743 B1 | 11/2002 | Kirkpatrick et al. |
| 6,491,940 B1 | 12/2002 | Levin |
| 6,526,318 B1 | 2/2003 | Ansarinia |
| 6,529,774 B1 | 3/2003 | Greene |
| 6,531,454 B1 | 3/2003 | Leary et al. |
| 6,587,719 B1 | 7/2003 | Barrett et al. |
| 6,587,724 B2 | 7/2003 | Mann |
| 6,591,137 B1 | 7/2003 | Fischell et al. |
| 6,591,138 B1 | 7/2003 | Fischell et al. |
| 6,597,953 B2 | 7/2003 | Boling et al. |
| 6,597,954 B1 | 7/2003 | Pless et al. |
| 6,606,521 B2 | 8/2003 | Paspa et al. |
| 6,609,025 B2 | 8/2003 | Barrett et al. |
| 6,609,032 B1 | 8/2003 | Woods et al. |
| 6,609,956 B2 | 8/2003 | Margaria |
| 6,618,623 B1 | 9/2003 | Pless et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,647,296 B2 | 11/2003 | Fischell et al. |
| 6,662,035 B2 | 12/2003 | Sochor |
| 6,678,553 B2 | 1/2004 | Lerner et al. |
| 6,690,974 B2 | 2/2004 | Archer et al. |
| 6,810,285 B2 | 10/2004 | Pless et al. |
| 6,811,788 B2 | 11/2004 | Yu |
| 6,853,850 B2 | 2/2005 | Shim et al. |
| 6,853,858 B2 | 2/2005 | Shalev |
| 6,905,827 B2 | 6/2005 | Wohlgemuth et al. |
| 2001/0004644 A1 | 6/2001 | Levin |
| 2002/0026652 A1 | 2/2002 | Allen et al. |
| 2002/0044919 A1 | 4/2002 | Yu |
| 2002/0068080 A1 | 6/2002 | Lerner |
| 2002/0082583 A1 | 6/2002 | Lerner |
| 2002/0099412 A1 | 7/2002 | Fischell et al. |
| 2002/0123678 A1 | 9/2002 | Lerner et al. |
| 2002/0133841 A1 | 9/2002 | Leviten |
| 2002/0169307 A1 | 11/2002 | Klein |
| 2002/0169485 A1 | 11/2002 | Pless et al. |
| 2002/0183683 A1 | 12/2002 | Lerner |
| 2003/0005473 A1 | 1/2003 | Brennan et al. |
| 2003/0005477 A1 | 1/2003 | Leviten |
| 2003/0013136 A1 | 1/2003 | Balser et al. |
| 2003/0014772 A1 | 1/2003 | Allen |
| 2003/0018988 A1 | 1/2003 | Allen et al. |
| 2003/0018989 A1 | 1/2003 | Brennan et al. |
| 2003/0051268 A1 | 3/2003 | Allen |
| 2003/0056238 A1 | 3/2003 | Wisotzkey |
| 2003/0073917 A1 | 4/2003 | Echauz et al. |
| 2003/0074033 A1 | 4/2003 | Pless et al. |
| 2003/0106083 A1 | 6/2003 | Allen |
| 2003/0131367 A1 | 7/2003 | Guenther et al. |
| 2003/0133877 A1 | 7/2003 | Levin |
| 2003/0144711 A1 | 7/2003 | Pless et al. |
| 2003/0149457 A1 | 8/2003 | Tcheng et al. |
| 2003/0166099 A1 | 9/2003 | Sabbadini et al. |
| 2003/0166279 A1 | 9/2003 | Sabbadini et al. |
| 2003/0172390 A1 | 9/2003 | Wisotzkey et al. |
| 2003/0176892 A1 | 9/2003 | Shalev |
| 2003/0176898 A1 | 9/2003 | Gross et al. |
| 2003/0177514 A1 | 9/2003 | Leviten |
| 2003/0190601 A1 | 10/2003 | Sabbadini et al. |
| 2003/0190683 A1 | 10/2003 | Sabbadini et al. |
| 2003/0190749 A1 | 10/2003 | Surber et al. |
| 2003/0191426 A1 | 10/2003 | Lerner et al. |
| 2003/0194714 A1 | 10/2003 | Sabbadini et al. |
| 2003/0195588 A1 | 10/2003 | Fischell et al. |
| 2003/0195602 A1 | 10/2003 | Boling |
| 2003/0198995 A1 | 10/2003 | Sabbadini et al. |
| 2003/0198996 A1 | 10/2003 | Surber et al. |
| 2003/0199005 A1 | 10/2003 | Sabbadini et al. |
| 2003/0199088 A1 | 10/2003 | Sabbadini et al. |
| 2003/0199089 A1 | 10/2003 | Surber et al. |
| 2003/0202937 A1 | 10/2003 | Sabbadini et al. |
| 2003/0203411 A1 | 10/2003 | Sabbadini et al. |
| 2003/0203481 A1 | 10/2003 | Surber et al. |
| 2003/0207833 A1 | 11/2003 | Berkley et al. |
| 2003/0211086 A1 | 11/2003 | Berkley et al. |
| 2003/0211599 A1 | 11/2003 | Sabbadini et al. |
| 2003/0219408 A1 | 11/2003 | Sabbadini et al. |
| 2003/0219888 A1 | 11/2003 | Segall et al. |
| 2003/0224369 A1 | 12/2003 | Surber et al. |
| 2003/0224444 A1 | 12/2003 | Sabbadini et al. |
| 2003/0232335 A1 | 12/2003 | Surber et al. |
| 2004/0015068 A1 | 1/2004 | Shalev et al. |
| 2004/0033491 A1 | 2/2004 | Alsobrook, II et al. |
| 2004/0054297 A1 | 3/2004 | Wingeier et al. |
| 2004/0136950 A1 | 7/2004 | Ni et al. |
| 2004/0136951 A1 | 7/2004 | Ni et al. |
| 2004/0153129 A1 | 8/2004 | Pless et al. |
| 2004/0210269 A1 | 10/2004 | Shalev et al. |
| 2004/0220644 A1 | 11/2004 | Shalev et al. |
| 2005/0020519 A1 | 1/2005 | Albiston et al. |
| 2005/0074506 A1 | 4/2005 | Natan et al. |
| 2005/0112090 A9 | 5/2005 | Ni et al. |
| 2005/0118187 A1 | 6/2005 | Yu |
| 2005/0137646 A1 | 6/2005 | Wallace et al. |

| 2005/0137647 | A1 | 6/2005 | Wallace et al. |
| 2005/0159790 | A1 | 7/2005 | Shalev |
| 2005/0177514 | A1 | 8/2005 | Sasselli |
| 2005/0266099 | A1 | 12/2005 | Shalev |
| 2006/0020299 | A1 | 1/2006 | Shalev |

FOREIGN PATENT DOCUMENTS

| WO | WO 99/03473 | 1/1999 |
| WO | WO 00/44432 | 8/2000 |
| WO | WO 01/43733 | 6/2001 |
| WO | WO 03/063959 A1 | 8/2003 |

OTHER PUBLICATIONS

Branston, "The physiology of the cerebrovascular parasympathetic innervation", British Journal of Neurosurgery 9:319-329(1995).

Branston et al., "Contribution of cerebrovascular parasympathetic and sensory innervation to the short-term control of blood flow in rat cerebral cortex," J Cereb Blood Flow Metab 15(3):525-31 (1995).

Delephine et al, "Plasma protein extravasation induced in the dura mater by stimulation of the parasympathetic sphenopalatine ganglion", *Exp Neurol* 147(2):389-400 (1997).

Fusco et al, "Capsaicin-sensitive' sensory neurons in cluster headache: pathophysiological aspects and therapeutic indication", *Headache* 34(3):132-137 (1994).

Hara et al, "Parasympathetic cerebrovascular innervation: an anterograde tracing from the sphenopalatine ganglion in the rat", *Neurosurgery* 32(5):822-827 (1993).

Kroll et al, "Outwitting the blood-brain barrier for therapeutic purposes: osmotic opening and other means", *Neurosurgery* 42(5):1083-1099 (1998).

Lambert et al, "Decreased carotid arterial resistance in cats in response to trigeminal stimulation", *J Neurosurg* 61(2):307-315 (1984).

Masini et al., "Stimulation and resection of vidian nerve in patients with chronic hypertrophic non-allergic rhinitis: effect on histamine content in nasal mucosa," Agents and Actions 18:251-3 (1986).

Lee et al, "Drug transporters in the central nervous system: brain barriers and brain parenchyma considerations", *Pharmacol Rev* 53(4):569-596 (2001).

Major et al, "Odorants presented to the rat nasal cavity increase cortical blood flow", *Chem Senses* 24(6):665-669 (1999).

Rucci et al., "Effects of vidian nerve stimulation on the nasal and maxillary sinus mucosa," The Journal of Laryngology and Otology 98:597-607 (1984).

Rucci et al., "Histamine release from nasal mucosal mast cells in patients with chronic hypertrophic non-allergic rhinitis, after parasympathetic nerve stimulation," Agents Actions 25:314-20 (1988).

Rucci et al., "Tympanometric variations induced by vidian nerve stimulation in humans," The Journal of Laryngology and Otology 99:355-358 (1985).

Rucci L et al., "Vidian nerve resection in chronic hypertrophic non allergic rhinitis: effects on histamine content, number and rate of degranulation processes of mast cells in nasal mucosa," Rhinology 23:309-314 (1985).

Ruskell GL, "The orbital branches of the pterygopalatine ganglion and their relationship with internal carotid nerve branches in primates," *J Anat* 106(2):323-339 (1970).

Samad et al, "Interleukin-1 β-mediated induction of Cox-2 in the CNS contributes to inflammatory pain hypersensitivity", *Nature* 410(6827):471-475 (2001).

Sanders et al, "Efficacy of sphenopalatine ganglion blockade in 66 patients suffering from cluster headache: a 12- to 70-month follow-up evaluation", *Neurosurg* 87(6):876-880 (1997).

Seylaz et al., "Effect of stimulation of the sphenopalatine ganglion on cortical blood flow in the rat," J Cereb Blood Flow Metab 8:875-8 (1988).

Silver WL, "Neural and pharmacological basis for nasal irritation", *Ann N Y Acad Sci* 641:152-163 (1992).

Suzuki et al, "Selective electrical stimulation of postganglionic cerebrovascular parasympathetic nerve fibers originating from the sphenopalatine ganglion enhances cortical blood flow in the rat", *J Cereb Blood Flow Metab* 10(3):383-391 (1990).

Suzuki et al, "Effect on cortical blood flow of electrical stimulation of trigeminal cerebrovascular nerve fibres in the rat", *Acta Physiol Scand* 138(3):307-316 (1990).

Suzuki et al., in "Origins and pathways of cerebrovascular vasoactive intestinal polypeptide-positive nerves in rat," J Cereb Blood Flow Metab 8:697-712 (1988).

van de Waterrbeemd et al, "Estimation of blood-brain barrier crossing of drugs using molecular size and shape, and H-bonding descriptors", *J Drug Target* 6(2):151-165 (1998).

Toda et al., "Cerebral vasodilation induced by stimulation of the pterygopalatine ganglion and greater petrosal nerve in anesthetized monkeys," Neuroscience 96(2):393-398 (2000).

Toda et al., "Preganglionic and postganglionic neurons responsible for cerebral vasodilation mediated by nitric oxide in anesthetized dogs," J Cereb Blood Flow Metab 20:700-708 (2000).

Young, "Electrical stimulation of the trigeminal nerve root for the treatment of chronic facial pain," J Neurosurg 83:72-78 (1995).

U.S. Appl. No. 60/265,008, filed Jan. 30, 2001, Whitehurst et al.

METHOD AND APPARATUS FOR STIMULATING THE SPHENOPALATINE GANGLION TO MODIFY PROPERTIES OF THE BBB AND CERBRAL BLOOD FLOW

FIELD OF THE INVENTION

The present invention relates generally to medical procedures and electronic devices. More specifically, the invention relates to the use of electrical devices for implantation in the head, for example, in the nasal cavity. The invention also relates to apparatus and methods for administering drugs, for treating stroke and migraine, and for improving cerebral blood flow.

BACKGROUND OF THE INVENTION

The blood-brain barrier (BBB) is a unique feature of the central nervous system (CNS) which isolates the brain from the systemic blood circulation. To maintain the homeostasis of the CNS, the BBB prevents access to the brain of many substances circulating in the blood.

The BBB is formed by a complex cellular system of endothelial cells, astroglia, pericytes, perivascular macrophages, and a basal lamina. Compared to other tissues, brain endothelia have the most intimate cell-to-cell connections: endothelial cells adhere strongly to each other, forming structures specific to the CNS called "tight junctions" or zonula occludens. They involve two opposing plasma membranes which form a membrane fusion with cytoplasmic densities on either side. These tight junctions prevent cell migration or cell movement between endothelial cells. A continuous uniform basement membrane surrounds the brain capillaries. This basal lamina encloses contractile cells called pericytes, which form an intermittent layer and probably play some role in phagocytosis activity and defense if the BBB is breached. Astrocytic end feet, which cover the brain capillaries, build a continuous sleeve and maintain the integrity of the BBB by the synthesis and secretion of soluble growth factors (e.g., gamma-glutamyl transpeptidase) essential for the endothelial cells to develop their BBB characteristics.

Because of the BBB, certain non-surgical treatments of the brain based upon systemic introduction of compounds through the bloodstream have been ineffective or less effective. For example, chemotherapy has been relatively ineffective in the treatment of CNS metastases of systemic cancers (e.g., breast cancer, small cell lung cancer, lymphoma, and germ cell tumors), despite clinical regression and even complete remission of these tumors in non-CNS systemic locations. The most important factors determining drug delivery from blood into the CNS are lipid solubility, molecular mass, and electrical charge. A good correlation exists between the lipid solubility of a drug, expressed as the octanol/water partition coefficient, and the drug's ability to penetrate or diffuse across the BBB. This is particularly relevant for drugs with molecular weights smaller than 600 Da. The normal BBB prevents the passage of ionized water soluble drugs with a molecular weight greater than 180 dalton (Da). Most currently-available effective chemotherapeutic agents, however, have a molecular weight between 200 and 1200 Da. Therefore, based both on their lipid solubilities and molecular masses, the passage of many agents is impeded by the BBB.

In addition to transcellular diffusion of lipophilic agents, there are several specific transport mechanisms to carry certain molecules across the brain's endothelial cells. Specific transport proteins exist for required molecules, such as glucose and amino acids. Additionally, absorptive endocytosis and transcytosis occur for cationized plasma proteins. Specific receptors for certain proteins, such as transferrin and insulin, mediate endocytosis and transport across the cell.

Non-surgical treatment of neurological disorders is generally limited to systemic introduction of compounds such as neuropharmaceuticals and other neurologically-active agents that might remedy or modify neurologically-related activities and disorders. Such treatment is limited, however, by the relatively small number of known compounds that pass through the BBB. Even those that do cross the BBB often produce adverse reactions in other parts of the body or in non-targeted regions of the brain.

There have been a number of different studies regarding efforts to cross the BBB—specifically, with regard to overcoming the limited access of drugs to the brain. Such efforts have included, for example, chemical modification, development of more hydrophobic analogs, or linking an active compound to a specific carrier. Transient opening of the BBB in humans has been achieved by intracarotid infusion of hypertonic mannitol solutions or bradykinin analogs. Also, modulation of the P-glycoprotein, whose substrates are actively pumped out of brain cells into capillary lumens, has been found to facilitate the delivery of drugs to the brain. However, due to the inherent limitations of each of the aforementioned procedures, there is still a need for more generic, effective, and predictable ways to cross the BBB.

It would also be desirable to develop controllable means for modulating cerebral blood flow. Many pathological conditions, such as stroke, migraine, and Alzheimer's disease, are significantly affected or exacerbated by abnormal cerebral blood flow.

The following references, which are incorporated herein by reference, may be useful:

Delepine L, Aubineau P, "Plasma protein extravasation induced in the rat dura mater by stimulation of the parasympathetic sphenopalatine ganglion", *Experimental Neurology*, 147:389–400 (1997).

Hara H, Zhang Q J, Kuroyanagi T, Kobayashi S, "Parasympathetic cerebrovascular innervation: An anterograde tracing from the sphenopalatine ganglion in the rat", *Neurosurgery*, 32:822–827 (1993).

Jolliet-Riant P, Tillement J P, "Drug transfer across the blood-brain barrier and improvement of brain delivery", *Fundamental and Clinincal Pharmacology*, 13:16–25 (1999).

Kroll R A, Neuwelt E A, "Outwitting the blood brain barrier for therapeutic purposes: Osmotic opening and other means", *Neurosurgery*, 42:1083–1100 (1998).

Sanders M, Zuurmond W W, "Efficacy of sphenopalatine ganglion blockade in 66 patients suffering from cluster headache: A 12–70 month follow-up evaluation", *Journal of Neurosurgery*, 87:876–880 (1997).

Syelaz J, Hara H, Pinard E, Mraovitch S, MacKenzie E T, Edvinsson L, "Effects of stimulation of the sphenopalatine ganglion on cortical blood flow in the rat", *Journal of Cerebral Blood Flow and Metabolism*, 8:875–878 (1988).

Van de WaterbeemdH, Camenisch G, Folkers G, Chretien J R, Raevsky O A, "Estimation of blood brain barrier crossing of drugs using molecular size and shape and h bonding descriptors", *Journal of Drug Targeting*, 6:151–165 (1998).

Suzuki N, Hardebo J E, Kahrstrom J, Owman C, "Selective electrical stimulation of postganglionic cerebrovascular parasympathetic nerve fibers originating from the sphenopalatine ganglion enhances cortical blood flow in the rat", *Journal of Cerebral Blood Flow and Metabolism*, 10:383–391 (1990).

Suzuki N, Hardebo J E, Kahrstrom J, Owman C H, "Effect on cortical blood flow of electrical stimulation of trigeminal cerebrovascular nerve fibres in the rat", *Acta Physiologica Scandinavica*, 138:307–315 (1990).

OBJECTS OF THE INVENTION

It is an object of some aspects of the present invention to provide improved methods and apparatus for delivery of compounds to the brain, particularly through the BBB.

It is also an object of some aspects of the present invention to provide such methods and apparatus as can be employed to deliver such compounds through the BBB with a minimally invasive approach.

It is a further object of some aspects of the present invention to provide such methods and apparatus as can facilitate delivery of large molecular weight compounds through the BBB.

It is yet a further object of some aspects of the present invention to provide cost-effective methods and apparatus for delivery of compounds through the blood-brain-barrier.

It is still a further object of some aspects of the present invention to provide improved methods and apparatus for remedying or modifying neurological activities and disorders via delivery of compounds through the blood-brain-barrier.

It is also a further object of some aspects of the present invention to modulate cerebral blood flow.

It is an additional object of some aspects of the present invention to provide improved methods and apparatus for treating stroke.

It is yet an additional object of some aspects of the present invention to provide improved methods and apparatus for treating migraine.

It is still an additional object of some aspects of the present invention to provide improved methods and apparatus for treating neurological diseases (for example, Alzheimer's disease), whose prognosis and evolution of pathological symptoms are influenced by cerebral blood flow.

It is also an object of some aspects of the present invention to provide implantable apparatus which affects a property of the brain, without actually being implanted in the brain. In particular, the apparatus may be implanted in the nasal cavity.

These and other objects of the invention will become more apparent from the description of preferred embodiments thereof provided hereinbelow.

SUMMARY OF THE INVENTION

In preferred embodiments of the present invention, an electrical stimulator drives current into the sphenopalatine ganglion (SPG) or into neural tracts originating or reaching the SPG. Typically, the stimulator drives the current in order to control and/or modify SPG-related behavior, e.g., in order to induce changes in cerebral blood flow and/or to modulate permeability of the blood-brain barrier (BBB). These embodiments may be used in many medical applications, such as, by way of illustration and not limitation, (a) the treatment of cerebrovascular disorders such as stroke, (b) the treatment of migraine headaches, or (c) the facilitation of drug transport across the BBB.

It is to be appreciated that, whereas preferred embodiments of the present invention are described with respect to driving current into the SPG or into neural structures directly related thereto, the scope of the present invention includes driving current into other sites in the brain which upon stimulation modulate cerebral blood flow or modulate permeability properties of the BBB, as appropriate for a given application.

It is also to be appreciated that electrical "stimulation," as provided by preferred embodiments of the present invention, is meant to include substantially any form of current application to designated tissue, even when the current is configured to block or inhibit the activity of nerves.

It is further to be appreciated that implantation and stimulation sites, methods of implantation, and parameters of stimulation are described herein by way of illustration and not limitation, and that the scope of the present invention includes other possibilities which would be obvious to someone of ordinary skill in the art who has read the present patent application.

It is yet further to be appreciated that while preferred embodiments of the invention are generally described herein with respect to electrical transmission of power and electrical stimulation of tissue, other modes of energy transport may be used as well.

Such energy includes, but is not limited to, direct or induced electromagnetic energy, RF transmission, ultrasonic transmission, optical power, and low power laser energy (via, for example, a fiber optic cable).

It is additionally to be appreciated that whereas preferred embodiments of the present invention are described with respect to application of electrical currents to tissue, this is to be understood in the context of the present patent application and in the claims as being substantially equivalent to applying an electrical field, e.g., by creating a voltage drop between two electrodes.

The SPG is a neuronal center located in the brain behind the nose. It consists of parasympathetic neurons innervating the middle cerebral and anterior cerebral lumens, the facial skin blood vessels, and the lacrimal glands. Activation of this ganglion is believed to cause vasodilation of these vessels. A second effect of such stimulation is the opening of pores in the vessel walls, causing plasma protein extravasation (PPE). This effect allows better transport of molecules from within these blood vessels to surrounding tissue.

The middle and anterior cerebral arteries provide the majority of the blood supply to the cerebral hemispheres, including the frontal and parietal lobes in their entirety, the insula and the limbic system, and significant portions of the following structures: the temporal lobes, internal capsule, basal ganglia and thalamus. These structures are involved in many of the neurological and psychiatric diseases of the brain, and preferred embodiments of the present invention are directed towards providing improved blood supply and drug delivery to these structures.

There is also some animal evidence for the presence of SPG-originated parasympathetic innervation in the posterior cerebral and basilar arteries. Consistent with the assumption that this is also the case in humans, many regions of the human brain are within the reach of treatments provided by preferred embodiments of the present invention, as described hereinbelow.

Currently the SPG is a target of manipulation in clinical medicine, mostly in attempted treatments of severe headaches such as cluster headaches. The ganglion is blocked either on a short-term basis, by applying lidocaine, or permanently, by ablation with a radio frequency probe. In both cases the approach is through the nostrils. In some preferred embodiments of the present invention, similar methods for approaching the SPG are utilized, to enable the electrical stimulation or electrical blocking thereof.

According to a preferred embodiment of the instant invention, a method and apparatus are provided to enhance delivery of therapeutic molecules across the BBB by stimulation of the SPG and/or its outgoing parasympathetic tracts and/or another parasympathetic center. The apparatus typically stimulates the parasympathetic nerve fibers of the SPG, thereby inducing the middle and anterior cerebral arteries to dilate, and also causing the walls of these cerebral arteries walls to become more permeable to large molecules. In this manner, the movement of large pharmaceutical molecules from within blood vessels to the cerebral tissue is substantially increased. Preferably, therefore, this method can serve as a neurological drug delivery facilitator, without the sacrifices in molecular weight required by techniques of the prior art. In general, it is believed that substantially all pharmacological treatments aimed at cerebral cells for neurological and psychiatric disorders are amenable for use with these embodiments of the present invention. In particular, these embodiments may be adapted for use in the treatment of disorders such as brain tumors, epilepsy, Parkinson's disease, Alzheimer's disease, multiple sclerosis, schizophrenia, depression, stress, anxiety, and any other CNS disorders that are directly or indirectly affected by changes in cerebral blood flow or by BBB permeability changes.

Advantageously (and even in the absence of BBB permeability changes), patients with these and other disorders are generally helped by the vasodilation secondary to stimulation of the SPG, and the resultant improvement in oxygen supply to neurons and other tissue. For some applications, this treatment is given on a long-term basis, e.g., in the chronic treatment of Alzheimer's patients. For other applications, the treatment is performed on a short-term basis, e.g., to minimize the damage following an acute stroke event and initiate neuronal and therefore functional rehabilitation.

Blocking of nerve transmission in the SPG or in related neural tracts is used in accordance with some preferred embodiments of the present invention to treat or prevent migraine headaches.

There is therefore provided, in accordance with a preferred embodiment of the present invention, apparatus for modifying a property of a brain of a patient, including:

one or more electrodes, adapted to be applied to a site selected from a group of sites consisting of: a sphenopalatine ganglion (SPG) of the patient and a neural tract originating in or leading to the SPG; and a control unit, adapted to drive the one or more electrodes to apply a current to the site capable of inducing an increase in permeability of a blood-brain barrier (BBB) of the patient.

There is also provided, in accordance with a preferred embodiment of the present invention, apparatus for modifying a property of a brain of a patient, including:

one or more electrodes, adapted to be applied to a site selected from a group of sites consisting of: a sphenopalatine ganglion (SPG) of the patient and a neural tract originating in or leading to the SPG;

and a control unit, adapted to drive the one or more electrodes to apply a current to the site capable of inducing an increase in cerebral blood flow of the patient.

There is further provided, in accordance with a preferred embodiment of the present invention, apparatus for modifying a property of a brain of a patient, including:

one or more electrodes, adapted to be applied to a site selected from a group of sites consisting of: a sphenopalatine ganglion (SPG) of the patient and a neural tract originating in or leading to the SPG;

and a control unit, adapted to drive the one or more electrodes to apply a current to the site capable of inducing a decrease in cerebral blood flow of the patient.

There is still further provided, in accordance with a preferred embodiment of the present invention, apparatus for modifying a property of a brain of a patient, including:

one or more electrodes, adapted to be applied to a site selected from a group of sites consisting of: a sphenopalatine ganglion (SPG) of the patient and a neural tract originating in or leading to the SPG;

and a control unit, adapted to drive the one or more electrodes to apply a current to the site capable of inhibiting parasympathetic activity of the SPG.

Preferably, the one or more electrodes are adapted for a period of implantation in the patient greater than about one month.

In a preferred embodiment, the apparatus includes a wire, adapted to connect the control unit to the one or more electrodes, wherein the control unit is adapted to drive the one or more electrodes from a position external to the patient.

Alternatively or additionally, the control unit is adapted to drive the one or more electrodes by wireless communication from a position external to the patient. In a preferred embodiment, the apparatus includes an electromagnetic coupling, adapted to couple the control unit and the one or more electrodes. Alternatively or additionally, the control unit is adapted to be in electro-optical communication with the one or more electrodes. Further alternatively or additionally, the control unit is adapted to be in electro-acoustic communication with the one or more electrodes. Still further alternatively or additionally, the control unit is adapted to be implanted in a nasal cavity of the patient.

Preferably, the one or more electrodes are adapted to be implanted in a nasal cavity of the patient. For some applications, at least one of the one or more electrodes includes a flexible electrode, adapted for insertion through a nostril of the patient and to extend therefrom to the site.

The apparatus preferably includes at least one biosensor, adapted to measure a physiological parameter of the patient and to generate a signal responsive thereto. The control unit, in turn, is preferably adapted to modify a parameter of the applied current responsive to the signal. As appropriate, the biosensor may include one or more of the following:

a blood flow sensor.
a temperature sensor.
a chemical sensor.
an ultrasound sensor.
transcranial Doppler (TCD) apparatus.
laser-Doppler apparatus.
a systemic blood pressure sensor.
an intracranial blood pressure sensor.
a detecting element adapted to be fixed to a cerebral blood vessel, and wherein the control unit is adapted to analyze the signal to detect an indication of a change in blood pressure indicative of a clot.
a kinetics sensor (in this case, the control unit is typically adapted to analyze the signal to detect an indication of a change in body disposition of the patient).
an electroencephalographic (EEG) sensor.
a blood vessel clot detector.

In a preferred embodiment, the control unit is adapted to configure the current so as to facilitate uptake of a drug through the BBB when the permeability of the BBB is increased.

Alternatively or additionally, the control unit is adapted to configure the current so as to increase a diameter of a blood vessel and allow an embolus that is located at a site in the blood vessel to move from the site in the blood vessel.

Further alternatively or additionally, the control unit is adapted to drive the one or more electrodes to apply the current responsive to an indication of stroke.

Still further alternatively or additionally, the control unit is adapted to drive the one or more electrodes to apply the current responsive to an indication of migraine of the patient.

There is also provided, in accordance with a preferred embodiment of the present invention, a method for modifying a property of a brain of a patient, including:

selecting a site from a group of sites consisting of: a sphenopalatine ganglion (SPG) of the patient and a neural tract originating in or leading to the SPG; and applying a current to the site capable of inducing an increase in permeability of a blood-brain barrier (BBB) of the patient.

There is additionally provided, in accordance with a preferred embodiment of the present invention, a method for modifying a property of a brain of a patient, including:

selecting a site from a group of sites consisting of: a sphenopalatine ganglion (SPG) of the patient and a neural tract originating in or leading to the SPG; and applying a current to the site capable of inducing an increase in cerebral blood flow of the patient.

There is yet additionally provided, in accordance with a preferred embodiment of the present invention, a method for modifying a property of a brain of a patient, including:

selecting a site from a group of sites consisting of: a sphenopalatine ganglion (SPG) of the patient and a neural tract originating in or leading to the SPG;

and applying a current to the site capable of inducing a decrease in cerebral blood flow of the patient.

There is still additionally provided, in accordance with a preferred embodiment of the present invention, a method for modifying a property of a brain of a patient, including: selecting a site from a group of sites consisting of: a sphenopalatine ganglion (SPG) of the patient and a neural tract originating in or leading to the SPG;

and applying a current to the site capable of inhibiting parasympathetic activity of the SPG.

For some applications, the one or more electrodes are adapted for a period of implantation in the patient less than about one week.

There is further provided, in accordance with a preferred embodiment of the present invention, vascular apparatus, including:

a detecting element, adapted to be fixed to a blood vessel of a patient and to generate a signal responsive to energy coming from the blood vessel; and a control unit, adapted to analyze the signal so as to determine an indication of an embolus in the blood vessel.

Preferably, the detecting element includes an energy transmitter and an energy receiver. For example, the energy transmitter may include an ultrasound transmitter or a transmitter of electromagnetic energy.

There is yet further provided, in accordance with a preferred embodiment of the present invention, a method for detecting, including:

fixing a detecting element to a blood vessel of a patient; generate a signal responsive to energy coming from the blood vessel; and analyzing the signal so as to determine an indication of an embolus in the blood vessel.

The present invention will be more fully understood from the following detailed description of the preferred embodiments thereof, taken together with the drawings, in which:

DETAILED DESCRIPTION OF THE INVENTION

Figure 1:
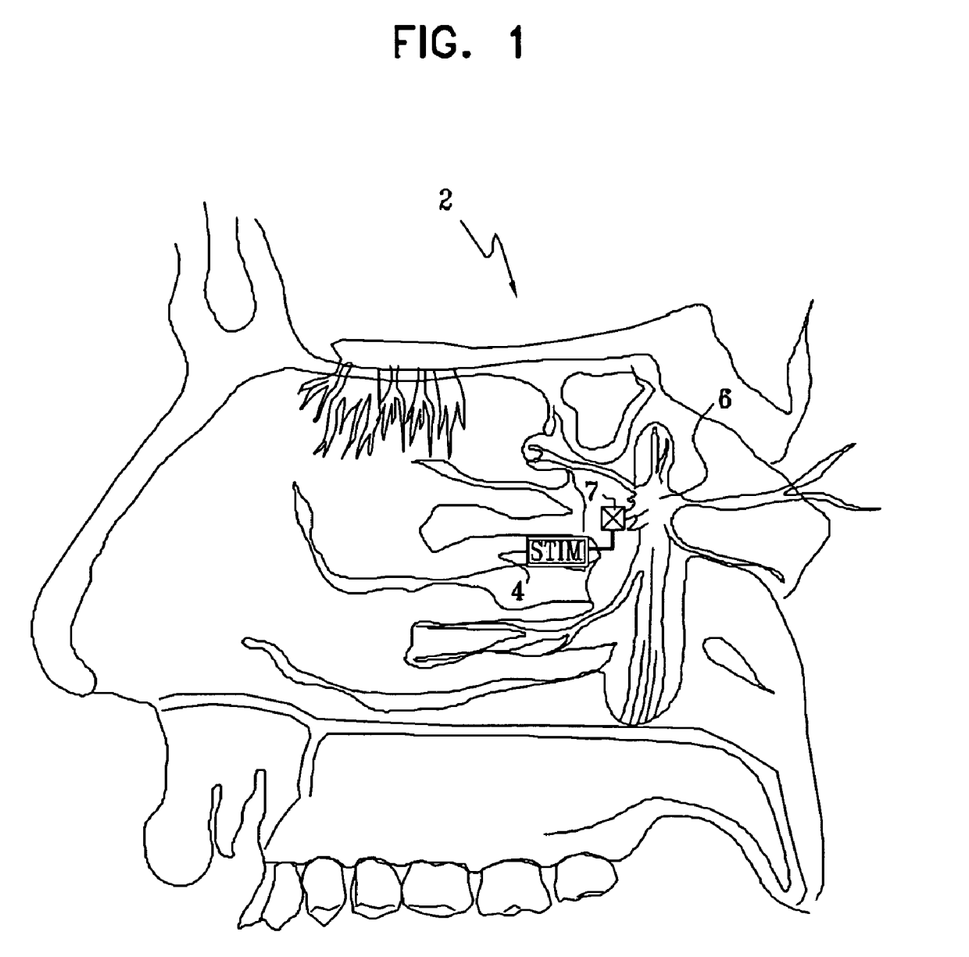
FIG. 1 is a schematic pictorial view of a fully implantable stimulator for stimulation of the SPG, in accordance with a preferred embodiments of the present invention.

FIG. 1 is a schematic pictorial view of a fully-implantable stimulator 4, for stimulation of the sphenopalatine ganglion (SPG) 6 or other parasympathetic site of a patient, in accordance with a preferred embodiments of the present invention. In FIG. 1, a human nasal cavity 2 is shown, and stimulator 4 is implanted adjacent to SPG 6. Branches of parasympathetic neurons coming from SPG 6 extend to the middle cerebral and anterior cerebral arteries (not shown). Preferably, one or more relatively short electrodes 7 extend from stimulator 4 to contact or to be in a vicinity of SPG 6 or of nerves innervating SPG 6 (e.g., postganglionic parasympathetic trunks thereof).

For some applications, stimulator 4 is implanted on top of the bony palate, in the bottom of the nasal cavity. Alternatively or additionally, the stimulator is implanted at the lower side of the bony palate, at the top of the oral cavity. In this instance, one or more flexible electrodes 7 originating in the stimulator are passed through the palatine bone or posterior to the soft palate, so as to be in a position to stimulate the SPG or its parasympathetic tracts. Further alternatively or additionally, the stimulator may be directly attached to the SPG and/or to its postganglionic parasympathetic trunk(s).

For some applications, stimulator 4 is delivered to a desired point within nasal cavity 2 by removably attaching stimulator 4 to the distal end of a rigid or slightly flexible introducer rod (not shown) and inserting the rod into one of the patient's nasal passages until the stimulator is properly positioned. As appropriate, the placement process may be facilitated by fluoroscopy, x-ray guidance, fine endoscopic surgery (FES) techniques or by any other effective guidance method known in the art, or by combinations of the aforementioned. Preferably, the ambient temperature and/or cerebral blood flow is measured concurrently with insertion. The cerebral blood flow may be measured with, for example, a laser Doppler unit positioned at the patient's forehead or transcranial Doppler measurements. Verification of proper implantation of the electrodes onto the appropriate neural structure may be performed by activating the device, and generally simultaneously monitoring cerebral blood flow.

The passage of certain molecules from cerebral blood vessels into the brain is hindered by the BBB. The endothelium of the capillaries, the plasma membrane of the blood vessels, and the foot processes of the astrocytes all impede uptake by the brain of the molecules. The BBB generally allows only small molecules (e.g., hydrophilic molecules of molecular weight less than about 200 Da, and lipophilic molecules of less than about 500 Da) to pass from the circulation into the brain.

In accordance with a preferred embodiment of the present invention, parasympathetic activation induced by current from stimulator 4 overcomes the resistance to trans-BBB molecular movement generated by the endothelium of the cerebral capillaries and the plasma membrane. For some applications, therefore, stimulator 4 may be used to transiently remove a substantial obstacle to the passage of drugs from the blood to the brain. For example, the stimulator may cyclically apply current for about two minutes, and subsequently have a rest period of between about 1 and 20 minutes.

It is hypothesized that two neurotransmitters play an important role in this change in properties of the BBB—vasoactive intestinal polypeptide (VIP) and nitric oxide (NO). (Acetylcholine may also be involved.) VIP is a short peptide, and NO is a gaseous molecule. VIP is believed to be a major factor in facilitating plasma protein extravasation (PPE), while NO is responsible for vasodilation. For some applications, stimulator 4 is adapted to vary parameters of the current applied to the SPG, as appropriate, in order to selectively influence the activity of one or both of these neurotransmitters. For example, stimulation of the parasympathetic nerve at different frequencies can induce differential secretion—low frequencies cause secretion of NO, while high frequencies (e.g., above about 10 Hz) cause secretion of peptides (VIP).

For other applications, a constant level DC signal, or a slowly varying voltage ramp is applied, in order to block parasympathetic neural activity in affected tissue. Alternatively, similar results can be obtained by stimulating at a rate higher than about 10 Hz, because this tends to exhaust neurotransmitters. Thus, stimulator 4 may be configured to induce parasympathetic electrical block, in order to cause vasoconstriction by mimicking the overall effect of chemical block on the SPG. This vasoconstrictive effect may be used, for example, to controllably prevent or reverse the formation of migraine headaches. This technique of electrical treatment of migraines stands in contrast to methods of the prior art, in which pharmacological agents such as lidocaine are used to induce SPG block.

Figure 2:
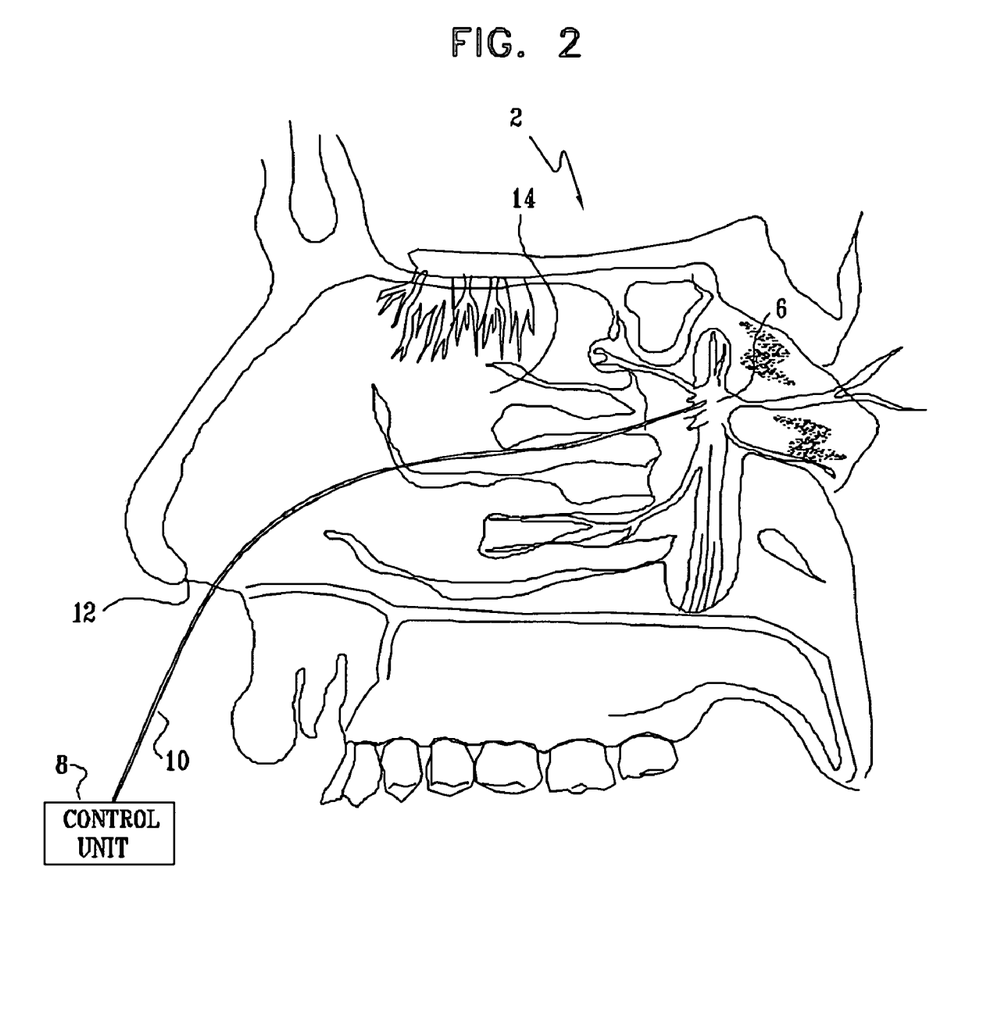
FIG. 2 is a schematic pictorial view of another stimulator for stimulation of the SPG, in accordance with a preferred embodiment of the present invention.

FIG. 2 is a schematic illustration of a stimulator control unit 8 positioned external to a patient's body, in accordance with a preferred embodiment of the present invention. At least one flexible electrode 10 preferably extends from control unit 8, through a nostril 12 of the patient, and to a position within the nasal cavity 14 that is adjacent to SPG 6.

It is to be understood that electrodes 7 (FIG. 1) and 10 may each comprise one or more electrodes, e.g., two electrodes, or an array of microelectrodes. For applications in which stimulator 4 comprises a metal housing that can function as an electrode, then typically one electrode 7 is used, operating in a monopolar mode. Regardless of the total number of electrodes in use, typically only a single or a double electrode extends to SPG 6. Other electrodes 7 or 10 or a metal housing of stimulator 4 are preferably temporarily or permanently implanted in contact with other parts of nasal cavity 2.

Each of electrodes 7 and/or 10 preferably comprises a suitable conductive material, for example, a physiologically-acceptable material such as silver, iridium, platinum, a platinum iridium alloy, titanium, nitinol, or a nickel-chrome alloy. For some applications, one or more of the electrodes have lengths ranging from about 1 to 5 mm, and diameters ranging from about 50 to 100 microns. Each electrode is preferably insulated with a physiologically-acceptable material such as polyethylene, polyurethane, or a co-polymer of either of these. The electrodes are preferably spiral in shape, for better contact, and may have a hook shaped distal end for hooking into or near the SPG. Alternatively or additionally, the electrodes may comprise simple wire electrodes, spring-loaded "crocodile" electrodes, or adhesive probes, as appropriate.

In a preferred embodiment of the invention, each one of electrodes 7 and/or 10 comprises a substantially smooth surface, except that the distal end of each such electrode is configured or treated to have a large surface area. For example, the distal tip may be porous platinized. Alternatively or additionally, at least the tip of electrode 7 or 10, and/or a metal housing of stimulator 4 includes a coating comprising an anti-inflammatory drug, such as beclomethasone sodium phosphate or beclomethasone phosphate. Alternatively, such an anti-inflammatory drug is injected or otherwise applied.

Figure 3:
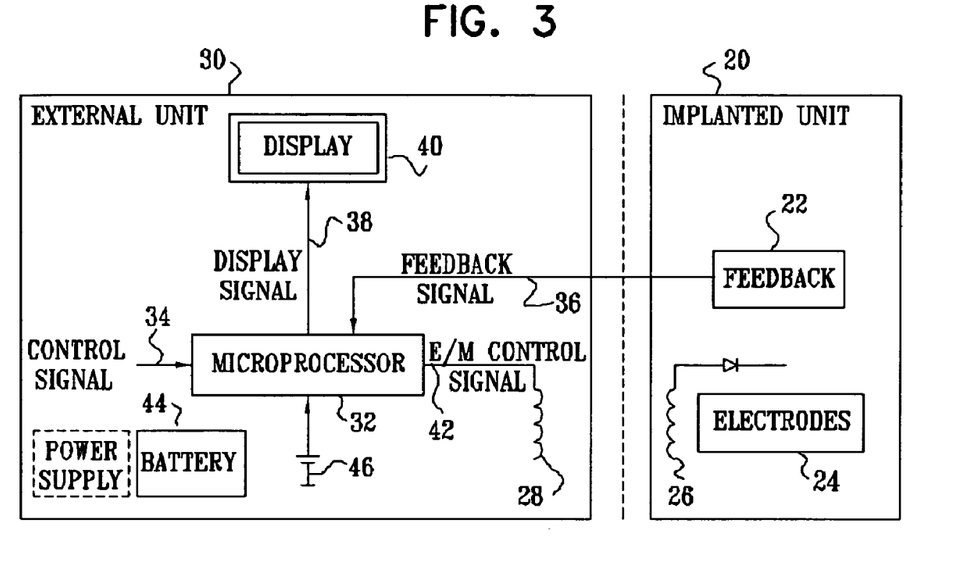
FIG. 3 is a schematic block diagram illustrating circuitry for use with the stimulator shown in FIG. 1, in accordance with a preferred embodiment of the present invention.

FIG. 3 is a schematic block diagram illustrating circuitry comprising an implanted unit 20 and an external unit 30, for use with stimulator 4 (FIG. 1), in accordance with a preferred embodiment of the present invention. Implanted unit 20 preferably comprises a feedback block 22 and one or more sensing or signal application electrodes 24. Implanted unit 20 typically also comprises an electromagnetic coupler 26, which receives power and/or sends or receives data signals to or from an electromagnetic coupler 28 in external unit 30.

External unit 30 preferably comprises a microprocessor 32 which receives an external control signal 34 (e.g., from a physician or from the patient), and a feedback signal 36 from feedback block 22. Control signal 34 may include, for example, operational parameters such as a schedule of operation, patient parameters such as the patient's weight, or signal parameters, such as desired frequencies or amplitudes of a signal to be applied to the SPG. If appropriate, control signal 34 can comprise an emergency override signal, entered by the patient or a healthcare provider to terminate stimulation or to modify it in accordance with a predetermined program. Microprocessor 32, in turn, preferably processes control signal 34 and feedback signal 36 so as to determine one or more parameters of the electric current to be applied through electrodes 24. Responsive to this determination, microprocessor 32 typically generates an electromagnetic control signal 42 that is conveyed by electromagnetic coupler 28 to electromagnetic coupler 26. Control signal 42 preferably corresponds to a desired current or voltage to be applied by electrodes 24 to SPG 6, and, in a preferred embodiment, inductively drives the electrodes. The configuration of couplers 26 and 28 and/or other circuitry in units 20 or 30 may determine the intensity, frequency, shape, monophasic or biphasic mode, or DC offset of the signal (e.g., a series of pulses) applied to designated tissue.

Power for microprocessor 32 is typically supplied by a battery 44 or, optionally, another DC power supply. Grounding is provided by battery 44 or a separate ground 46. If appropriate, microprocessor 32 generates a display signal 38 that drives a display block 40 of external unit 30. Typically, but not necessarily, the display is activated to show feedback data generated by feedback block 22, or to provide a user interface for the external unit.

Implanted unit 20 is preferably packaged in a case made of titanium, platinum or an epoxy or other suitable biocompatible material. Should the case be made of metal, then the case may serve as a ground electrode and, therefore, stimulation typically is performed in a monopolar mode. Alternatively, should the case be made of biocompatible plastic material, two electrodes 24 are typically driven to apply current to the SPG.

For some applications, the waveform applied by one or more of electrodes 24 to designated tissue (e.g., the SPG) comprises a waveform with an exponential decay, a ramp up or down, a square wave, a sinusoid, a saw tooth, a DC component, or any other shape known in the art to be suitable for application to tissue. Alternatively or additionally, the waveform comprises one or more bursts of short shaped or square pulses—each pulse preferably less than about 1 ms in duration. Generally, appropriate waveforms and parameters thereof are determined during an initial test period of external unit 30 and implanted unit 20. For some applications, the waveform is dynamically updated according to measured physiological parameters, measured during a period in which unit 20 is stimulating the SPG, and/or during a non-activation (i.e., standby) period.

In the case of migraine treatment, the waveform may take the form of a slowly varying shape, such as a slow saw tooth, or a constant DC level, intended to block outgoing parasympathetic messaging.

Figure 4:
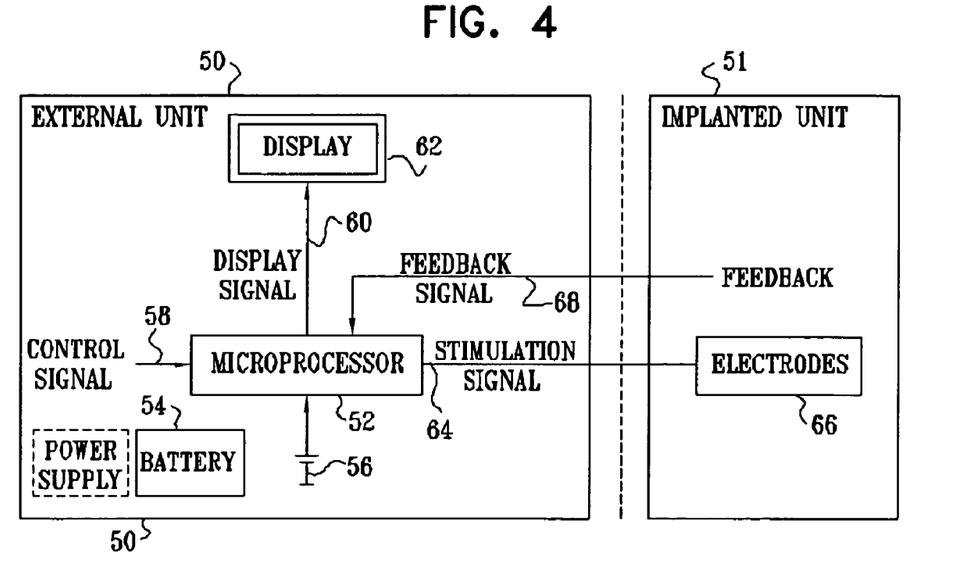
FIG. 4 is a schematic block diagram illustrating circuitry for use with the stimulator shown in FIG. 2, in accordance with a preferred embodiment of the present invention.

FIG. 4 is a schematic block diagram of circuitry for use, for example, in conjunction with control unit 8 (FIG. 2), in accordance with a preferred embodiment of the present invention. An external unit 50 comprises a microprocessor 52 supplied by a battery 54 or another DC power source. Grounding may be provided by battery 54 or by a separate ground 56. Microprocessor 52 preferably receives control and feedback signals 58 and 68 (analogous to signal 34 and 36 described hereinabove), and generates responsive thereto a stimulation signal 64 conveyed by one or more electrodes 66 to the SPG or other tissue. Typically, but not necessarily, feedback signal 68 comprises electrical feedback measured by one or more of electrodes 66 and/or feedback from other sensors on or in the patient's brain or elsewhere coupled to the patient's body. If appropriate, microprocessor 52 generates a display signal 60 which drives a display block 62 to output relevant data to the patient or the patient's physician.

Typically, some or all of electrodes 66 are temporarily implanted in the patient (e.g., following a stroke), and are directly driven by wires connecting the external unit to the implanted unit.

Figure 5A:
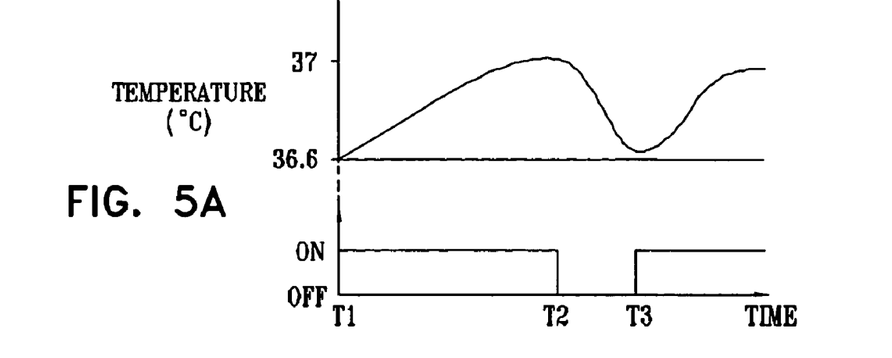
FIGS. 5A and 5B are schematic illustrations depicting different modes of operation of stimulators such as those shown in FIGS. 1 and 2, in accordance with preferred embodiments of the present invention.

FIG. 5A is a graph schematically illustrating a mode of operation of one or more of the devices shown in FIGS. 1–4, in accordance with a preferred embodiment of the present invention. Preferably, the effect of the applied stimulation is monitored by means of a temperature transducer at the SPG or elsewhere in the head, e.g., in the nasal cavity. As shown in FIG. 5A for a step (ON/OFF) mode of stimulation, stimulation of the SPG or related tissue is initiated at a time T1, and this is reflected by a measurable rise in temperature (due to increased blood flow). Once the temperature rises to a predetermined or dynamically-varying threshold (e.g., 37° C.), stimulation is terminated (time T2), responsive to which the temperature falls. As appropriate, when the temperature drops to a designated or dynamically-determined point, the stimulation is reinitiated (time T3). Preferably, suitable temperatures or other physiological parameters are determined for each patient so as to provide the optimal treatment. If appropriate, control instructions may also be received from the patient, e.g., to initiate stimulation upon the onset of a migraine headache.

Figure 5B:
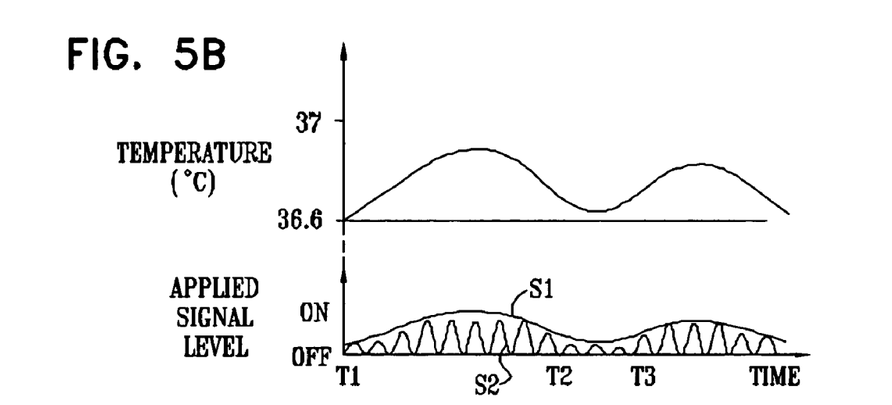

FIG. 5B is a graph schematically illustrating a mode of operation of one or more of the devices shown in FIGS. 1–4, in accordance with another preferred embodiment of the present invention. In this embodiment, the amplitude of the waveform applied to the SPG is varied among a continuous set of values (sol), or a discrete set of values (S2), responsive to the measured temperature, in order to achieve the desired performance. It will be appreciated that other feedback parameters measured in the head (e.g., intracranial pressure and/or cerebral blood flow), as well as measured systemic parameters (e.g., heart rate) and subjective patient inputs (e.g., migraine pain=3/5) may be used in conjunction with or separately from temperature measurements, in order to achieve generally optimal performance of the implanted apparatus.

Figure 6:
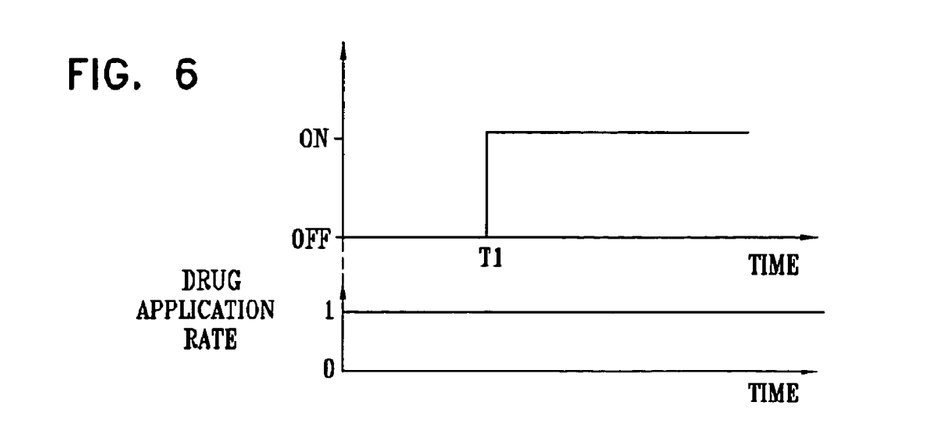
FIG. 6 is a schematic illustration of a mode of operation of the stimulators shown in FIGS. 1 and 2, synchronized with a drug delivery system, in accordance with a preferred embodiment of the present invention.

FIG. 6 is a graph schematically illustrating a mode of operation of one or more of the devices shown in FIGS. 1–4, in accordance with a preferred embodiment of the present invention. In this embodiment, a drug is administered to the patient at a constant rate, e.g., intravenously, prior to the initiation of stimulation of the SPG at time T1. Advantageously, this prior generation of heightened concentrations of the drug in the blood tends to provide relatively rapid transfer of the drug across the BBB and into the brain, without unnecessarily prolonging the enhanced permeability of the BBB while waiting for the blood concentration of the drug to reach an appropriate level. Alternatively, for some applications it is desirable to give a single injection of a bolus of the drug shortly before or after initiation of stimulation of the SPG. Typically, combined administration and stimulation schedules are determined by the patient's physician based on the biochemical properties of each drug targeted at the brain.

Figure 7:
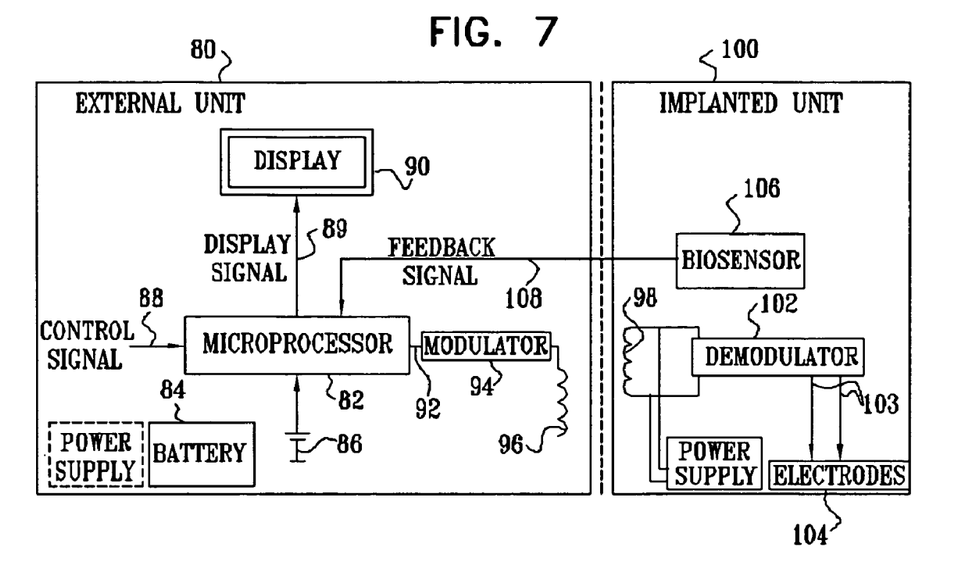
FIG. 7 is a schematic block diagram illustrating circuitry for use with the stimulator shown in FIG. 1, where the stimulator is driven by an external controller and energy source using a modulator and a demodulator, in accordance with a preferred embodiment of the present invention.

FIG. 7 is a schematic block diagram showing circuitry for parasympathetic stimulation, which is particularly useful in combination with the embodiment shown in FIG. 1, in accordance with a preferred embodiment of the present invention. An external unit 80 preferably comprises a microprocessor 82 that is powered by a battery 84 and/or an AC power source. Microprocessor 82 is grounded through battery 84 or through an optional ground 86.

In a typical mode of operation, an external control signal 88 is input to microprocessor 82, along with a feedback signal 108 from one or more biosensors 106, which are typically disposed in a vicinity of an implanted unit 100 or elsewhere on or in the patient's body. Responsive to signals 88 and 108, microprocessor 82 preferably generates a display signal 89 which drives a display 90, as described hereinabove. In addition, microprocessor 82 preferably processes external control signal 88 and feedback signal 108, to determine parameters of an output signal 92, which is modulated by a modulator 94. The output therefrom preferably drives a current through an electromagnetic coupler 96, which inductively drives an electromagnetic coupler 98 of implanted unit 100. A demodulator 102, coupled to electromagnetic coupler 98, in turn, generates a signal 103 which drives at least one electrode 104 to apply current to the SPG or to other tissue, as appropriate.

Preferably, biosensor 106 comprises implantable or external medical apparatus including, for example, one or more of the following:

- a blood flow sensor,
- a temperature sensor,
- a chemical sensor,
- an ultrasound sensor,
- transcranial Doppler (TCD) apparatus,
- laser-Doppler apparatus,
- a systemic or intracranial blood pressure sensor (e.g., comprising a piezoelectric crystal fixed to a major cerebral blood vessel, capable of detecting a sudden blood pressure increase indicative of a clot),
- a kinetics sensor, comprising, for example, an acceleration, velocity, or level sensor (e.g., a mercury switch), for indicating body dispositions such as a sudden change in body attitude (as in collapsing),
- an electroencephalographic (EEG) sensor comprising EEG electrodes attached to, or implanted in, the patients head, for indicating changes in neurological patterns, such as symptoms of stroke or migraine,
- a blood vessel clot detector (e.g., as described hereinbelow with reference to FIG. 13),
- or other monitors of physiological quantities suitable for carrying out the objects of this or other embodiments of the present invention.

Figure 8:
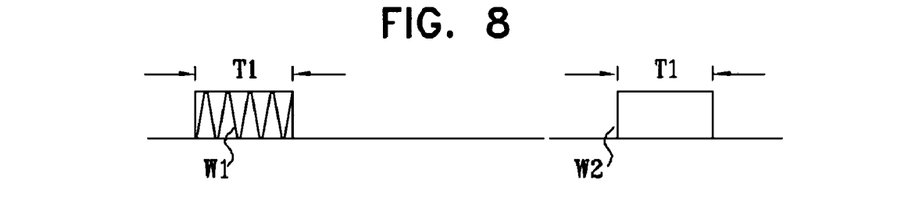
FIG. 8 depicts sample modulator and demodulator functions for use with the circuitry of FIG. 7, in accordance with a preferred embodiment of the present invention.

FIG. 8 is a schematic illustration showing operational modes of modulator 94 and/or demodulator 102, in accordance with a preferred embodiment of the present invention. The amplitude and frequency of signal 92 in FIG. 7 can have certain values, as represented in the left graph; however, the amplitude and frequency are modulated so that signal 103 has different characteristics.

Figure 9:
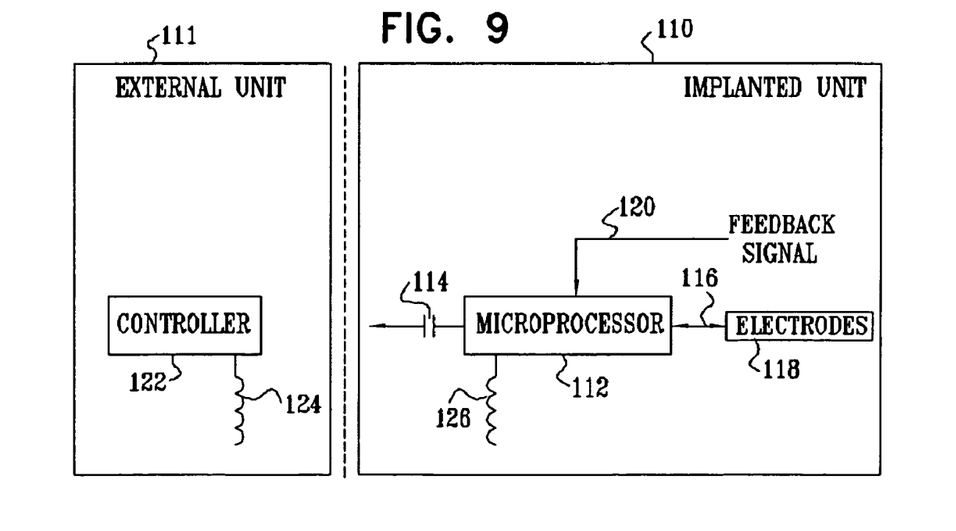
FIGS. 9, 10A, and 10B are schematic diagrams illustrating further circuitry for use with implantable stimulators, in accordance with respective preferred embodiments of the present invention.

FIG. 9 is a schematic illustration of further apparatus for stimulation of the SPG, in accordance with a preferred embodiment of the present invention. In this embodiment, substantially all of the processing and signal generation is performed by circuitry in an implanted unit 110 in the patient, and, preferably, communication with a controller 122 in an external unit 111 is performed only intermittently. The implanted unit 110 preferably comprises a microprocessor 112 coupled to a battery 114. Microprocessor 112 generates a signal 116 that travels along at least one electrode 118 to stimulate the SPG. A feedback signal 120 from a biosensor (not shown) and/or from electrode 118 is received by microprocessor 112, which is adapted to modify stimulation parameters responsive thereto. Preferably, microprocessor 112 and controller 122 are operative to communicate via electromagnetic couplers 126 and 124, in order to exchange data or to change parameters. Further preferably, battery 114 is inductively rechargeable by electromagnetic coupling.

Figure 10A:
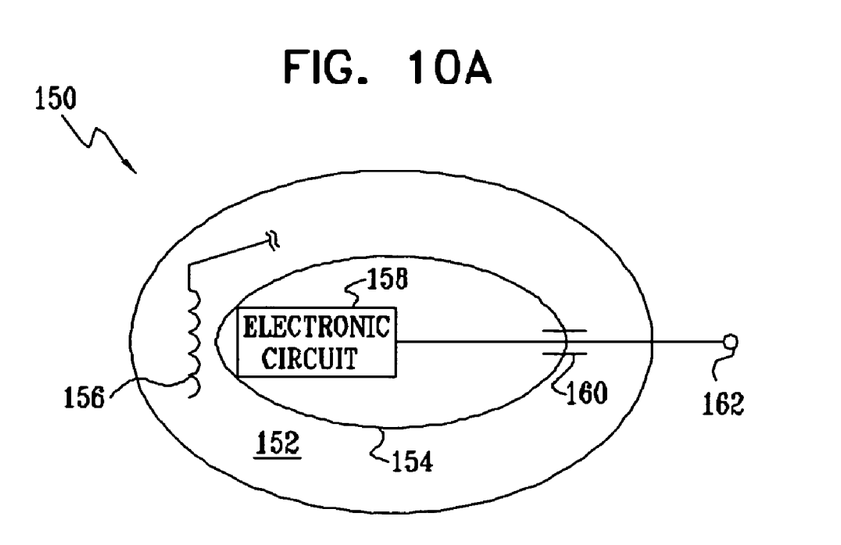

FIG. 10A is a schematic illustration of a stimulator 150, in accordance with a preferred embodiment of the present invention. Preferably, substantially all of the electronic components (including an electronic circuit 158 having a rechargeable energy source) are encapsulated in a biocompatible metal case 154. An inductive coil 156 and at least one electrode 162 are preferably coupled to circuit 158 by means of a feed-through coupling 160. The inductive coil is preferably isolated by an epoxy coating 152, which allows for higher efficiency of the electromagnetic coupling.

Figure 10B:
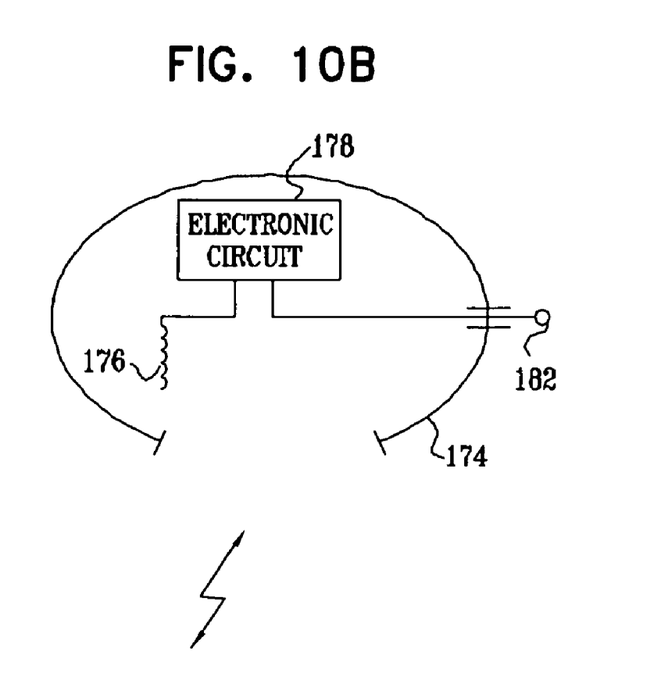

FIG. 10B is a schematic illustration of another configuration of an implantable stimulator, in accordance with a preferred embodiment of the present invention. Preferably, substantially all of the electronic components (including an inductive coil 176 and an electronic circuit 178 having a rechargeable energy source) are encapsulated in a biocompatible metal case 174. One or more feed-throughs are preferably provided to enable coupling between at least one electrode 182 and the electronic circuit, as well as between inductive coil 176 and another inductive coil (not shown) in communication therewith.

With reference to FIGS. 10A and 10B, the energy source for electronic circuits 158 and 178 may comprise, for example, a primary battery, a rechargeable battery, or a super capacitor. For applications in which a rechargeable battery or a super capacitor is used, any kind of energizing means may be used to charge the energy source, such as (but not limited to) standard means for inductive charging or a miniature electromechanical energy converter that converts the kinetics of the patient movement into electrical charge. Alternatively, an external light source (e.g., a simple LED, a laser diode, or any other light source) may be directed at a photovoltaic cell in the electronic circuit. Further alternatively, ultrasound energy is directed onto the implanted unit, and transduced to drive battery charging means.

Figure 11:
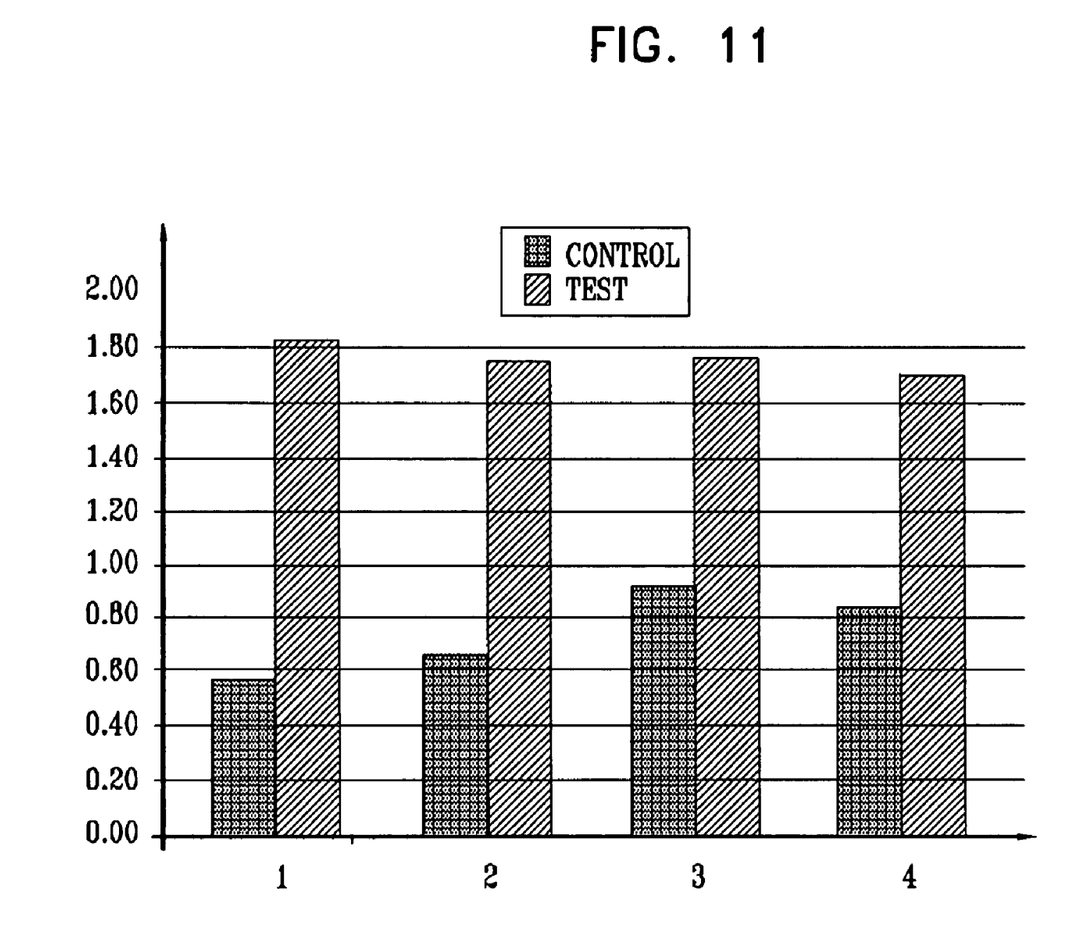
FIGS. 11 and 12 are bar graphs showing experimental data collected in accordance with a preferred embodiment of the present invention.
Figure 12:
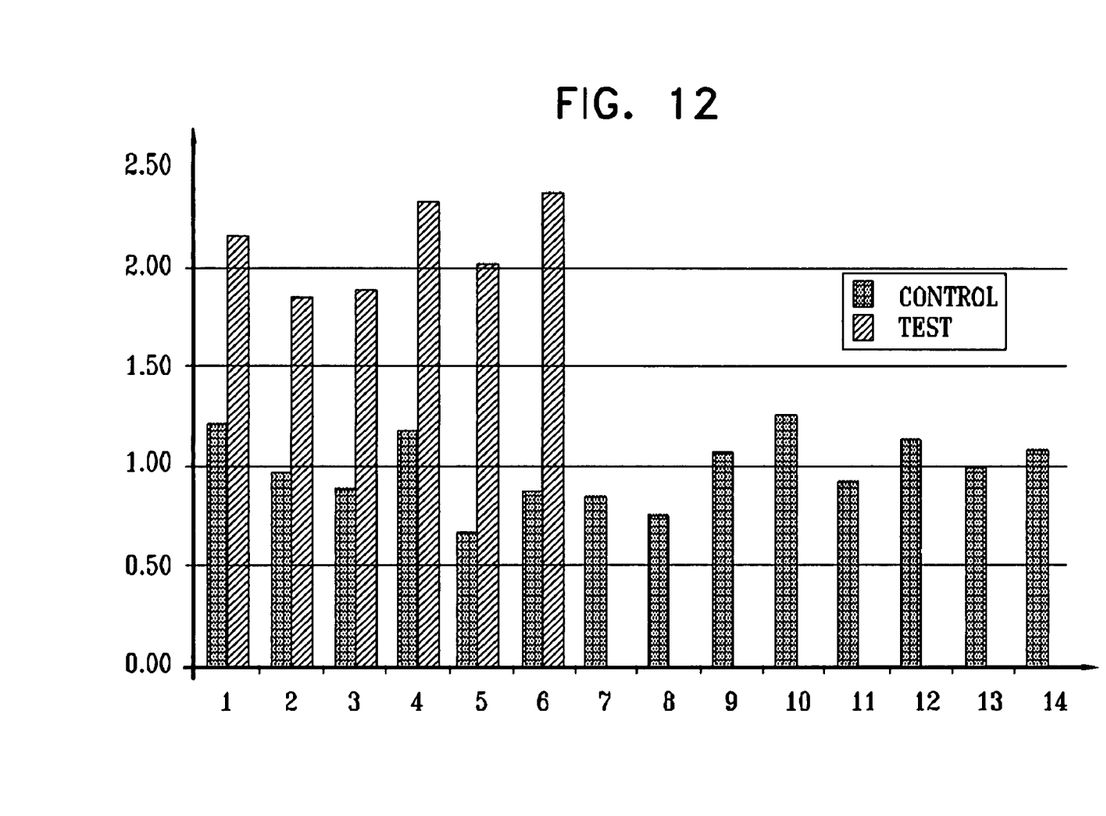

FIGS. 11 and 12 are bar graphs showing experimental results obtained during rat experiments performed in accordance with a preferred embodiment of the present invention. A common technique in monitoring bio-distribution of materials in a system includes monitoring the presence and level of radio-labeled tracers. These tracers are unstable isotopes of common elements (e.g., Tc, In, Cr, Ga, and Gd), conjugated to target materials. The chemical properties of the tracer are used as a predictor for the behavior of other materials with similar physiochemical properties, and are selected based on the particular biological mechanisms that are being evaluated. Typically, a patient or experimental animal is placed on a Gamma camera, or target tissue samples can be harvested and placed separately into a well counter. For the purpose of the present set of experiments which were performed, the well counter method was chosen due to its higher sensitivity and spatial resolution. A series of experiments using 99Tc-DTPA (DTPA molecule conjugated to a 99Technetium isotope) were performed. The molecular weight of 99Tc-DTPA is 458 Da, its lipophilicity is negative, and its electric charge is +1. These parameters are quite similar with pharmacological agents used in standard chemotherapy, such as tamoxifen, etoposide and irinotecan.

FIGS. 11 and 12 show results obtained using 99Tc-DTPA penetration assays using ordinary brain sampling techniques (FIG. 11) and peeled brain techniques (FIG. 12). The x-axis of each graph represents different experimental runs, and the y-axis of each graph is defined as: [(hemisphere radioactivity)/(hemisphere weight)/(total injected radioactivity)/(total animal weight)]. The results obtained demonstrate an average 2.5-fold increase in the penetration of 99Tc-DTPA to the rat brain. It is noted that these results were obtained by unilateral stimulation of the SPG. The inventors believe that bilateral SPG stimulation will approximately double drug penetration, relative to unilateral SPG stimulation.

In both FIG. 11 and FIG. 12, some animals were designated as control animals, and other animals were designated as test animals. In each group, the left and right hemispheres were tested separately, and the height of each bar represents, for a given animal and a given hemisphere, the normalized level of radioactivity as defined above. Thus, FIG. 11 shows results from a total of four test hemispheres and four control hemispheres. FIG. 12 shows results from six test hemispheres and fourteen control hemispheres. The juxtaposition of control and test bars in the bar graphs is not meant to imply pairing of control and test hemispheres.

Figure 13:
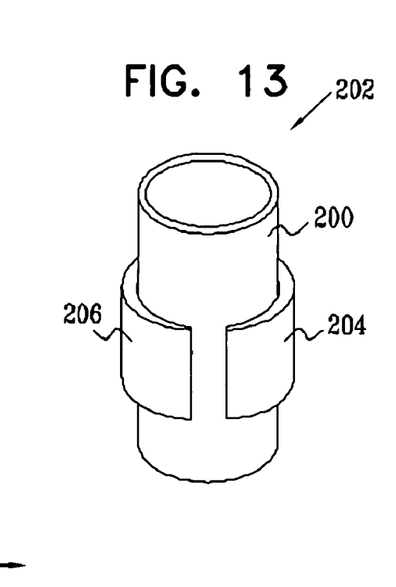
FIG. 13 is a schematic illustration of a sensor for application to a blood vessel, in accordance with a preferred embodiment of the present invention.

FIG. 13 is a schematic illustration of acoustic or optical clot detection apparatus 202, for use, for example, in providing feedback to any of the microprocessors or other circuitry described hereinabove, in accordance with a preferred embodiment of the present invention. The detection is preferably performed by coupling to a major blood vessel 200 (e.g., the internal carotid artery or aorta) a detecting element comprising an acoustic or optical transmitter/receiver 206, and an optional reflecting surface 204. Natural physiological liquids may serve as a mediating fluid between the device and the vessel. Preferably, the transmitter/receiver generates an ultrasound signal or electromagnetic signal which is reflected and returned, and a processor evaluates changes in the returned signal to detect indications of a newly-present clot. Alternatively, a transmitter is placed on one side of the vessel and a receiver is placed on the other side of the vessel. In either case, for some applications, more than one such apparatus 202 are placed on the vessel, in order to improve the probability of successful clot detection for possible estimation of the clot's direction of motion within the vessel, and to lower the false alarm (i.e., false detection) rate.

Embodiments of the present invention have many medical applications. For example, chemotherapeutic drugs need to pass into cerebral tissue in order to treat brain tumors. Most of the chemotherapeutic drugs have molecular weights of 200–1200 Da, and thus their transport through the blood-brain barrier (BBB) is highly restricted. To overcome the impedance of the BBB, an intracarotid infusion of high osmotic load has been used in the prior art in order to open the tight junctions of the BBB for a very short period (e.g., 25 minutes), during which the medications are given. This procedure is not simple—it is invasive, requires general anesthesia, requires subsequent intensive care, and is in any case relatively expensive. For these reasons, such intracarotid infusions are used only in very few healthcare facilities, even though some reports claim a substantial improvement in life expectancy in patients receiving chemotherapy in this manner.

Preferably, embodiments of the present invention which facilitate increased trans-BBB drug delivery, and therefore more efficient chemotherapy, also enable a reduction or elimination of the need for radiotherapy. It is noted that such irradiation of the brain is indicated in the literature to be a significant cause of long-term cognitive and other deficits.

The better delivery of drugs, as provided in accordance with a preferred embodiment of the present invention, is also a factor in the treatment of other disorders, such as Parkinson's disease, Alzheimer's disease, and other neurological diseases. For some applications, the trans-BBB delivery of various growth factors is facilitated using the techniques described herein. Growth factors are typically large molecules that stimulate the growth of neurons, and may be used to treat degenerative disorders, such as Parkinson's disease, Alzheimer's disease, and Motor Neuron Diseases (e.g., Lou Gehrig's disease).

Another preferred application of the present invention includes facilitating drug delivery across the BBB in order to treat inflammation in the brain, e.g., for cases of infectious diseases of the brain in immunocompromised patients. Similarly, medications to treat AIDS may be more effectively administered to sites in the brain through the BBB, when appropriate, through the use of methods and apparatus described herein. A further application of some embodiments of the present invention includes the delivery through the BBB of viruses that are agents of gene therapy (e.g., for treating Parkinson's disease). Similarly, methods and apparatus described herein may be used for metabolic disorders of the brain, such as GM2 gangliosidosis.

Another aspect of some preferred embodiments of the invention relates to the modulation of cerebral blood flow. Roughly 750,000 Americans suffer strokes each year. Stroke is the United States' third leading cause of death, killing about 160,000 Americans every year. More than 3 million people in the United States have survived strokes, of whom more than 2 million suffer crippling paralysis, speech loss and lapses of memory. About 85% of strokes are ischemic, i.e., a blood vessel is occluded and its territory is deprived of oxygen supply. A cerebral region that is totally deprived of blood supply is surrounded by a second region of partial lack of supply, whose vitality is at risk. This second region is one of the main targets of some embodiments of the invention-stimulation of the SPG will dilate its vessels and significantly improve that region's likelihood of survival. If the intervention is given early enough in the event (e.g., a few hours post-stroke), it might help also the core region of the stroke, as the thrombus is not yet organized, and dilation of the vessels may reintroduce blood supply to the tissue. Alternatively, SPG stimulation may allow the clot to move from a big vessel to a small vessel, and thus deprive blood supply only from a much smaller volume of the brain (which would, in any case, have probably been deprived of blood supply had the clot remained in place).

Population-based studies have shown that about 5% of men and 16% of women suffer migraine attacks. Over 80% of these people suffer some degree of headache-related disability. Parasympathetic block (in contrast to stimulation) is known to cause vasoconstriction. An embodiment of the present invention uses electrical means to induce the vasoconstrictive effect and treat migraine. For example, it may use techniques to block nerve messaging, such as applying a slowly-varying voltage, or in some cases, a constant level DC voltage.

Alzheimer's disease is becoming a major source of disability and financial load with the increase in life expectancy. In recent years, vascular factors have been considered prominent in the pathophysiology of the disease. Current therapy is generally concentrated along one line—cholinomimetic medications, which can, at most, slow down the deterioration of cognitive function in patients. SPG stimulation, as provided in accordance with a preferred embodiment of the present invention, is believed to increase blood flow and oxygen supply to the brain, and therefore help these patients. For this use, permanent stimulators may be implanted in the nasal cavity, for long-term intermittent stimulation.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description. For example, elements which are shown in a figure to be housed within one integral unit may, for some applications, be disposed in a plurality of distinct units. Similarly, apparatus for communication and power transmission which are shown to be coupled in a wireless fashion may be, alternatively, coupled in a wired fashion, and apparatus for communication and power transmission which are shown to be coupled in a wired fashion may be, alternatively, coupled in a wireless fashion.

What is claimed is:

1. A method for modifying a property of a brain of a patient, comprising:
   selecting a site from a group of sites consisting of: a sphenopalatine ganglion (SPG) of the patient and a neural tract originating in or leading to the SPG; and
   applying a current to the site capable of inducing an increase in permeability of a blood-brain barrier (BBB) of the patient.

2. A method according to claim 1, wherein selecting the site comprises implanting an electrode at the site, designated to remain in the patient for a period greater than about one month.

3. A method according to claim 1, wherein applying the current comprises implanting a control unit in a nasal cavity of the patient.

4. A method according to claim 1, wherein applying the current comprises implanting one or more electrodes in a nasal cavity of the patient.

5. A method according to claim 4, wherein implanting comprises inserting a flexible electrode through a nostril of the patient.

6. A method according to claim 1, and comprising sensing a physiological parameter of the patient and generating a signal responsive thereto, wherein applying the current comprises modifying a parameter of the applied current responsive to the signal.

7. A method according to claim 6, wherein sensing comprises sensing blood flow of the patient.

8. A method according to claim 6, wherein sensing comprises performing a transcranial Doppler (TCD) technique.

9. A method according to claim 6, wherein sensing comprises performing a laser Doppler technique.

10. A method according to claim 1, wherein applying the current comprises configuring the current so as to facilitate uptake of a drug through the BBB when the permeability of the BBB is increased.

11. A method according to claim 10, wherein the drug includes a chemotherapeutic drug, and wherein configuring the current comprises configuring the current so as to facilitate uptake of the chemotherapeutic drug through the BBB when the permeability of the BBB is increased.

12. A method according to claim 1, wherein selecting the site comprises implanting an electrode at the site, designated to remain in the patient for a period less than about one week.

13. A method according to claim 1, wherein applying the current comprises configuring the current so as to treat a condition of the patient.

14. A method according to claim 1, wherein applying the current comprises setting a parameter of the current, so as to induce the increase in permeability of the BBB.

15. A method according to claim 14, wherein the parameter includes a frequency of the current, and wherein setting the parameter comprises setting the frequency of the current, so as to induce the increase in permeability of the BBB.

16. A method according to claim 15, wherein setting the frequency comprises setting the frequency to be greater than about 10 Hz, so as to induce the increase in permeability of the BBB.

17. A method according to claim 14, wherein the parameter includes an amplitude of the current, and wherein setting the parameter comprises setting the amplitude of the current, so as to induce the increase in permeability of the BBB.

18. A method according to claim 14, wherein the parameter includes a waveform of the current, and wherein setting the parameter comprises setting the waveform of the current, so as to induce the increase in permeability of the BBB.

19. A method according to claim 18, wherein a shape of the waveform is selected from the list consisting of: an exponential decay, a ramp up or down, a square wave, a monophasic shape, a biphasic shape, a sinusoid, a saw tooth, and a DC component, and wherein setting the parameter comprises setting the waveform of the current, so as to induce the increase in permeability of the BBB.

20. A method according to claim 18, wherein the waveform includes one or more pulse bursts, and wherein setting the parameter comprises setting the waveform of the current, so as to induce the increase in permeability of the BBB.

21. A method according to claim 1, wherein applying the current comprises implanting a control unit at a site at a top of a bony palate of the patient.

22. A method according to claim 1, wherein applying the current comprises implanting a control unit at a site at a lower side of a bony palate of the patient.

23. A method according to claim 1, comprising administering, to a systemic blood circulation of the patient, a therapeutic agent for treating a medical condition, wherein applying the current comprises configuring the current so as to facilitate uptake of the therapeutic agent through the BBB when the permeability of the BBB is increased.

24. A method according to claim 23, wherein administering the therapeutic agent comprises commencing administration of the therapeutic agent prior to initiating the application of the current.

25. A method according to claim 23, wherein administering the therapeutic agent comprises administering the therapeutic agent shortly after initiating the application of the current.

26. A method according to claim 23, wherein the therapeutic agent includes large pharmaceutical molecules selected from the list consisting of: hydrophilic molecules having a molecular weight of greater than about 200 Da, and lipophilic molecules having a molecular weight of greater than about 500 Da, and wherein administering the therapeutic agent comprises administering the large pharmaceutical molecules.

27. A method according to claim 23, wherein the condition includes a brain tumor, and wherein administering the therapeutic agent comprises administering a drug for treating the brain tumor.

28. A method according to claim 23, wherein the therapeutic agent includes a chemotherapeutic drug, and wherein administering the therapeutic agent comprises administering the chemotherapeutic drug.

29. A method according to claim 1, wherein the site includes the SPG, and wherein applying the current to the site comprises applying the current to the SPG.

30. A method according to claim 1, wherein the site includes the neural tract originating in or leading to the SPG, and wherein applying the current to the site comprises applying the current to the neural tract originating in or leading to the SPG.

* * * * *